United States Patent [19]
Mauro et al.

[11] Patent Number: 5,968,827
[45] Date of Patent: Oct. 19, 1999

[54] CELLULAR AGGREGATE STABILIZED CULTURE AND PROCESS FOR THE DEVELOPMENT OF EMBRYOS FROM A PROEMBRYOGENIC STRAIN FOR USE IN VINE REGENERATION TECHNIQUES

[75] Inventors: Marie-Claude Mauro, Orbais-l'Abbaye; Alain Deloire, Reims; Pierre Coutos-Thevenot, Paris, all of France

[73] Assignee: Champagne Moet & Chandon, Epernay, France

[21] Appl. No.: 08/792,121

[22] Filed: Jan. 31, 1997

Related U.S. Application Data

[63] Continuation of application No. 08/335,766, filed as application No. PCT/FR93/00456, May 11, 1993, abandoned.

[30] Foreign Application Priority Data

May 12, 1992 [FR] France .................................. 92 05724

[51] Int. Cl.⁶ ...................................... C12N 5/04
[52] U.S. Cl. ......................... 435/410; 435/420; 800/200
[58] Field of Search ................................... 435/410, 420; 800/200

[56] References Cited

FOREIGN PATENT DOCUMENTS 0 255 083  7/1987  European Pat. Off. .
WO 85/03085  7/1985  WIPO .
WO 91/05854  5/1991  WIPO .

OTHER PUBLICATIONS

Journal American Society of Horticultural Science, vol. 113, No. 6, 1988, pp. 941–945, St. Joseph, Michigan, U.S., J.A. Stamp et al: "Proliferative Somatic Embryogenesis from Zygotic Embryos of Grapevine".

Plant Cell Reports, vol. 7, No. 8, 1989, pp. 684–687, Berlin, DE, N. Matsuta et al. "Embryogenic Cell Lines From Somatic Embryos of Grape (*Vitis vinifera* L.)".

Hortsience vol. 26, No. 6, p. 772, St. Joseph, Michigan, US D.J. Gray et al.: Perennial Embryogenic Cell Cultures of Grape—Grapevine Cell Culture; application to Somatic Embryogenesis (Conference Abstract).

Gray et al. *Hortscience* 26(6) 1991 p. <156>.

Matsuta et al. *Plant Cell Reports* (7) 1989 pp. 684–687.

Stamp et al. *J. Amer. Soc. Hort. Sci* 113(6) 1988 pp. 941–945.

*Primary Examiner*—Leon B. Lankford, Jr.
*Attorney, Agent, or Firm*—Pollock, Vande Sande & Amernick

[57] ABSTRACT

A stabilized culture of a proembryogenic cell line deposited under No. PL92042917 and variants and derived cultures having preserved comparable proembryogenic properties.

19 Claims, No Drawings

CELLULAR AGGREGATE STABILIZED CULTURE AND PROCESS FOR THE DEVELOPMENT OF EMBRYOS FROM A PROEMBRYOGENIC STRAIN FOR USE IN VINE REGENERATION TECHNIQUES

This application is a continuation of U.S. patent application Ser. No. 08/335,766, filed Jan. 31, 1995 now abandoned under 35 U.S.C. §371 as a national stage application of PCT/FR93/00456, filed May 11, 1993.

FIELD OF THE INVENTION

The present invention relates to the regeneration of vine by somatic embryogenesis and more particularly to a culture of proembryogenic cellular aggregates and to a process for developing embryos from these cultures.

BACKGROUND OF THE INVENTION

Vine regeneration, as a post-research technique, is of primary importance in the improvement of vines. Vine generation has a double objective in the wine quality and environmental protection fields. Regarding the latter aspect in particular, it is evident why it is very important to be able to regenerate and propagate, for example, plants that are resistant to certain diseases, so as to reduce the use of plant-protection products, which are often harmful to the environment.

With the aim of improving vine cultivars, while preserving the organoleptic characteristics of the products resulting therefrom, various in vitro culture and modification techniques have been tested especially so as to define early selection screens, as for example for resistance to diseases (BRANCHARD M., Agronomie, 1984 4 (9), 905–911) or for tolerance to the toxicity of certain elements in the soil (Bouquet A. et al., Symposium "Amélioration de la Vigne et Culture in vitro", (Vine improvement and in vitro culture), Paris, 1985, 147–157).

In order to develop such a vine regeneration technique, it is however necessary to have at least the following elements:

a stabilized culture of proembryogenic cells that can be replicated or modified genetically;

a culture medium and a technique allowing its replication and its maintenance; and a culture medium and a technique that promote the formation of embryos and their development into plantlets.

In the present description, "plantlet" will be used to designate a plant derived from a somatic embryo, by analogy with the actual plantlet normally derived from the germination of a zygotic embryo of the seed. Still more precisely, the term "plantlet" used in the present description designates the plant in the state where, after complete development of the embryo, well developed green cotyledons and root elongation are observed.

Various cultural processes had been developed for the replication of the proembryogenic cells and the development of the embryos, especially by the formation and the development of secondary embryos, as described in U.S. Pat. No. 4,532,733.

However, the techniques described are faced with many difficulties, both with respect to the formation of the embryos, which are generally abnormal, and the development into plantlets, the latter being as a result obtained with particularly low yields.

In particular, it has been observed that the formation of secondary embryos, which are often abnormal, in fact led to a reduction in the yield of developed, that is to say cotyledonary, embryos at the end of the culture. Thus, these difficulties did not allow the use of these techniques subsequent to applied research results to be envisaged for industrial production.

Moreover, as is easily evident, the higher the embryogenic power of the cells of the culture used, the higher the yields of developed embryos and of plantlets.

Stabilized culture is understood to mean a culture of cells, or of cellular aggregates, of which the quantity of DNA per cellular nucleus remains identical during the course of replications, and which produces by means of regeneration techniques a plant identical to the initial plant, it being possible for such a stability to extend beyond 4 years of culturing and regular subculturings.

The cells are mainly diploid with the exception of those undergoing mitosis which are, in this case, tetraploid.

Variant or derived culture is understood to mean the cells modified especially by mutations, chromosome rearrangements, genetic recombination or epigenetic phenomena.

Comparable proembryogenic properties is understood to mean a culture capable of developing at least 100 embryos per mg of cells.

SUMMARY OF THE INVENTION

The present invention, therefore, relates, firstly, to a stabilized culture of proembryogenic cellular aggregates deposited on Apr. 29, 1992 under No. PL92042917 at the ECACC collection (European Collection of Animal Cell Cultures—Division of Biologies—Porton Down—Salisbury, Wiltshire, SP4 0JG, UK), their variants and the derived cultures, in particular those having preserved comparable proembryogenic properties.

The culture deposited under No. PL92042917 ECACC is a strain of embryogenic cells, in the form of cellular aggregates, that is obtained from anthers of the rootstock 41B derived from a *Vitis vinifera* cv. Chasselasx *Vitis berlandieri* crossing.

DETAILED DESCRIPTION OF THE INVENTION

In order to culture and subculture these cells, it is necessary to have an appropriate liquid culture medium and technique so as to prevent the formation and the development of embryos, while permitting the mitoses.

Thus, the present invention also relates to a process for maintaining a strain of proembryogenic vine cells by means of a standard liquid medium for plant cell culture, such as for example a Murashige and Skoog (MS) or Nitsch and Nitsch medium, supplemented with auxin, at a sufficient concentration for inhibiting cellular differentiation into embryos, while permitting mitoses, and whose pH is between 5 and 6, adjusted, for example, with an aqueous solution of dilute sodium hydroxide.

Among the auxins, there may be mentioned 2,4-dichlorophenoxyacetic acid (2,4D), 1-naphthaleneacetic acid (NAA), 2-naphthoxyacetic acid (NOA).

It has however been observed that in the implementation of the process of the invention, the effect of the various auxins was more or less beneficial. Thus, the auxin 2,4D, although permitting good multiplication of the cells at the start of the culture, often and quite rapidly leads, after 2 or 3 weeks, to necroses, hence a very substantial drop in the viability of the cells. The action of ANA is different: on the one hand the multiplication of the cells is quite slow, and on the other a fairly large number of cells differentiate into embryos, which is obviously contrary to the desired aim.

On the other hand, it appears that NOA gives the best results.

Thus, according to an advantageous embodiment of the process of the invention mentioned above, 2-naphthoxyacetic acid (NOA) will be chosen as the auxin.

According to a variant of this embodiment, the NOA concentration in the culture medium is between 2.5 and 7.5 $\mu$M/liter and preferably it is about 5 $\mu$M/liter.

According to yet another embodiment of the process mentioned above, the said strain consisting of cellular aggregates is inoculated into the culture medium at a density of between about 3 and 8 mg of fresh cells per milliliter of medium. The culture is allowed to grow up to a density 3 to 5 times higher. Following which there is a return by subculturing to a subculture with a density substantially identical to that of the initial inoculation.

Preferably, prior to this subculture, the cellular aggregates are sieved so as to preserve for carrying out the subculture only those whose size does not exceed 500 $\mu$m.

If this sieving is not carried out, there would be a risk of cells differentiated to embryos appearing, which especially by virtue of the fact that the differentiation might have occurred in the presence of auxin, would lead to blocking of the development of the embryo at an early stage, and this in an irreversible manner.

According to a preferred variant of this embodiment, the abovementioned subculture is performed approximately every three weeks, whereas the culture medium is replaced each week by subculturing.

It appears that after four years, carrying out the procedure as indicated below, in such a medium, the culture No. PL92042917 ECACC developed while preserving its embryogenic power and its genetic stability.

It was thus observed that the abovementioned stabilized culture of the present invention made it possible to develop potentially 400 embryos per mg of cells whereas the prior art described an embryogenic potential of an embryo per mg (LEBRUN L. and BRANCHARD M., 3rd symposium on vine physiology, Bordeaux, 1989, 38–41).

Another aspect of the present invention relates to a process permitting the expression of this embryogenic power so as to obtain plantlets with yields compatible with an industrial exploitation, it being understood that these plantlets can be obtained only on the condition that the embryos can develop completely without giving rise to abnormalities, as in the case of the prior art processes.

Now, it has been found unexpectedly, that the replacement of the culture medium at regular intervals until plantlets are obtained made it possible to obtain such a result.

The present invention therefore also relates to a process for developing embryos from a proembryogenic strain intended for the regeneration of vine, in which the strain is cultured in an appropriate liquid culture medium replaced at regular intervals until plantlets are obtained in which two generally green well developed cotyledons and a long root can be distinguished.

The replacement of the culture medium is advantageously carried out by subculturing.

Advantageously, on each replacement of the medium or subculturing, the density of the culture is adjusted to the initial density for inoculation.

Generally and according to the density of the culture during inoculation, the strain is cultured between 3 and 7 days and then subcultured daily until plantlets are obtained.

The density of the culture during the inoculation is advantageously between 0.5 and 2 $\mu$l of sedimented cells (1×g) per ml of medium, preferably between 1 and 2 $\mu$l/ml. Thus, for a density of between 1 and 2 $\mu$l, the regular replacements of medium or subculturings will start between 3 and 4 days after the start of the culture, whereas they would be performed between the 5th and 6th day for lower densities.

Appropriate liquid culture medium is understood to mean a standard liquid medium for culturing plant cells free of auxin.

Preferably, this is a standard liquid medium, such as the Murashige and Skoog medium (1962) which is well known to persons skilled in the art, free of auxin and modified such that it contains only half the concentration of macroelements, that sucrose was replaced with glycerol and maltose and to which a casein hydrolysate was added.

In the process according to the invention, the strain advantageously consists, during the initial inoculation for initiation of the embryos, of cellular aggregates between 200 and 500 $\mu$m in size.

Such aggregates are obtained by culturing the strain, preferably by the above-described process for maintaining the strain in the presence of auxin, then they are filtered successively using a filter having a porosity of about 500 $\mu$m in order to remove the larger-size aggregates, then using a filter having a porosity of about 200 $\mu$m, so as to preserve only the cellular aggregates between 200 $\mu$m and 500 $\mu$m. Finally, these aggregates are washed preferably with the abovementioned appropriate culture medium so as to remove substantially all traces of auxin.

By carrying out the procedure according to the process of the invention, the embryos produced from the cellular aggregates pass successively through the following stages of development: globular, heart, torpedo and mature embryos or plantlets.

It may be advantageous, although not essential, to add to the culture medium a cytokinin, such as zeatin, from the moment when the embryos have reached the "torpedo" stage, so as to promote subsequent development. However, the duration of culture in the presence of cytokinin should not exceed the duration beyond which disturbances in the culture could appear.

This duration, for example for zeatin, is about 5 days.

As soon as the plantlets are obtained, they are transferred onto solid medium, for example agar, in the presence of an appropriate medium, so as to obtain developed plants.

The examples below make it possible to illustrate a preferred embodiment of the process according to the invention, applied to the culture deposited under No. PL92042917 ECACC, without however seeking to limit the scope thereof.

EXAMPLE 1

Maintenance of the Embryogenic Strain

The culture of cellular aggregates obtained from anthers of the rootstock 41B is maintained by culturing and regular subculturing in a standard liquid medium for culturing plant cells that is available commercially, such as a Murashige and Skoog (MS) medium supplemented with 2-naphthoxyacetic acid (NOA).

The cultures are performed in 250 ml Erlenmeyer flasks with 80 ml of medium, with stirring at about 110 rpm at 21° C., preferably in the dark.

The auxin concentration is 5 $\mu$M/l, and the pH is adjusted to 5.8 with 0.1N sodium hydroxide before autoclaving the medium at 120° C. for 20 minutes.

The strain is then inoculated at a density of between 3 and 8 mg of fresh cells per ml of medium and the culture is allowed to grow up to a density 3 to 5 times higher. The cellular aggregates are then sieved using a nylon screen having pores 500 μm in size so as to remove the larger-sized aggregates. The culture is subcultured in the supplemented MS medium each week.

The sieving procedure is repeated at regular intervals, approximately every two or three weeks, according to the density of the culture medium.

EXAMPLE 2

Initiation and Development of the Embryos

The culture medium used for the development of somatic embryos is a modified liquid MS culture medium comprising especially 18 g/l of maltose, and 4.6 g/l of glycerol replacing sucrose and 1 g/l of casein hydrolysate.

This auxin-free medium is used at a pH of 5.8, adjusted by the addition of 0.1N sodium hydroxide.

The culture medium is autoclaved for 20 min at 120° C. The undifferentiated cell cultures, obtained from the cell culture maintained according to the procedure of Example 1, are filtered successively through nylon screens having pores 500 μm, then 200 μm, in size so as to preserve for the inoculation of the culture only the cellular aggregates whose size is between these two values.

The undifferentiated cellular aggregates retained on the second filter are then washed 3 times with modified MS medium and then suspended in 30 ml of this medium.

The cell density expressed in μl of cell volume per ml of medium is determined after sedimentation (1×g) of the cells in a conical graduated tube.

80 ml of modified MS culture medium are then inoculated with a suspension of cellular aggregates at a density of 1 μl/ml in a 250 ml Erlenmeyer flask.

After culturing for 4 days, preferably in the dark, daily culturing is carried out in the modified MS medium until plantlets are obtained for an average period of 15 to 17 days.

The total duration for the development of the embryos going through the various globular, heart and then torpedo stages of development before giving a plantlet is about 20 days. After the appearance of the torpedo stage, about 10 to 12 days after starting the culture, there are added 5 mg/l of zeatin, a hormone that promotes the development of the cotyledons and the apex for a maximum period of 5 days.

The plantlets are then transferred into a solid agar medium (modified MS medium comprising half the concentration of micro- and macroelements 20 g/l of sucrose, 7 g/l of bacto-agar Difco, at pH 5.8) without any addition of growth regulator.

Developed plants are obtained by culturing the plantlets at 25° C., under a light intensity of 40 to 50 $\mu E.m^{-2}.s^{-1}$ (Mazda fluorescent tube fluo A9TFRS40/BI) with a photoperiod of 16 hours, for about 40 days.

This process, which is used several times with embryogenic cellular aggregates, makes it possible to obtain about 60% to 95% of plantlets compared with the number of embryos initially formed.

Comparative data between various processes for developing the embryos, with or without subculturing, are presented in Table 1.

TABLE I

| Conditions of transfer (1) | Stages of development (%) | | | | |
|---|---|---|---|---|---|
| | globular (2) | heart (3) | torpedo (4) | plantlet (5) | plant (6) |
| 20 days without subculturing | 40 | 60 | 0 | 0 | 0 |
| 4 days without subculturing + 16 daily subculturings | 0 | 1 | 8 | 91 | 80 |
| 10 days without subculturing + 16 daily subculturings | 17 | 68 | 15 | 0 | 0 |

All the trials were carried out using a composition of identical liquid medium and initial inoculation density.

Table I presents, on the one hand (columns 2 to 6), the number of embryos according to their stage of development per hundred embryos at the end of culture in liquid medium (20 days or 26 days). On the other, Table I presents (column 6) the number of normal developed plants, after forty days of culture on solid agar medium, per hundred plantlets transferred, as indicated above.

It can be noted that, according to the prior art processes, in the absence of daily subculturing (1st line of results) the embryos remain blocked at the "heart" stage, or even at the "globular" stage. On the other hand, according to the process of the invention (2nd line of results), with daily subculturing for 16 days, from the 4th day of culture, 91% of the embryos reached the "plantlet" stage, and are then capable of producing normal developed plants. On the other hand, it is observed (3rd line of results) that if the daily subculturing rates are not carried out sufficiently early, blocking of the development of the embryos occurs at the torpedo stage, and that no plantlet can thus be obtained.

Thus, by virtue of the process according to the invention, for one hundred embryos produced from the strain of embryogenic cellular aggregates, it is possible to obtain about 90 plantlets at the end of the culture in liquid medium and about 75 normal developed plants after transferring onto solid medium, thereby making this process compatible with industrial exploitation.

The developed plants obtained by the process described above are then planted, after their necessary adaptation to the external culture conditions, so as to obtain a regenerated vine.

The present invention therefore also relates to the vine regenerated by plants derived from plantlets obtained by the process described above.

Finally, when a stabilized culture of cellular aggregates exhibiting high embryogenic power, a medium appropriate for its maintenance and an effective process for developing the embryos are available, the whole can be used advantageously for the following applications:

- selection by screening of resistant plants, for example in the presence of a toxin;
- corresponding multiplication of the vine;
- production and fusion of protoplasts;
- transformation of the vine by mutagenesis; and
- transformation of the vine by genetic transformation.

This latter point is particularly important since the known genetic transformation examples are limited by the subsequent development of the transformed cells into embryos.

Indeed, in the techniques known for genetic transformation of vine, a blockage in the differentiation in embryos is observed for a good number of transformed cells. Thus, starting with a strain with high embryogenic power, a sufficient quantity of transformed embryos can generally be expected.

The present invention therefore also relates to the use of the stabilized culture deposited under No. PL92042917 ECACC, their variants and derived cultures, in particular those having preserved comparable proembryogenic properties for the transformation of the cells by an appropriate vector, followed by regeneration into a plant.

Appropriate vector is understood to mean any means permitting the transfer, integration into the genome, expression and replication of a gene inside a plant cell.

Among the known vectors, derivatives of Agrobacterium as described for example in European Patent No. 0,176,112 will be preferably used.

For the same reasons, the present invention also relates to the use of the stabilized culture deposited under No. PL92042917, and their variants and derived cultures, in particular those having preserved comparable proembryogenic properties, for the production of vine protoplasts.

The methods for the production of protoplasts that are described generally (Cell and Tissue Culture in Forestry, Vol. 2, Edit. JM. BONGA, Don J. DURZAN, Martines NIJHOFF Publishers 1987, DORDRECHT, BOSTON, LANCASTER), or more particularly for vine (BESSIS R. & al., workshop on the improvement of vine and in vitro culture, organized by MOET-HENNESSY S.A., PARIS, April 1985, p. 195–196; LEBRUN L., workshop on the improvement of vine and in vitro culture organized by MOET-HENNESSY S.A., PARIS, April 1985, p.215), will mainly be used.

We claim:

1. A stabilized culture of a proembryogenic cell line deposited under No. PL92042917 and variants and derived cultures having preserved comparable proembryogenic properties, wherein said culture can develop at least 100 embryos per mg of cells.

2. A process for maintaining a cell line of proembryogenic vine cells deposited under No. PL92042917 and variants and derived cultures having preserved comparable proembryogenic properties, wherein said culture can develop at least 100 embryos per mg of cells, comprising:

culturing said cells in a standard liquid culture medium for culturing plant cells, wherein said culture medium is supplemented with an auxin, wherein said culture medium is at a sufficient concentration for inhibiting cellular differentiation while permitting mitosis, and wherein the pH of said culture medium is between 5 and 6.

3. A process according to claim 2, further comprising the steps of:

inoculating said strain in to said culture medium at a density of between 3 and 8 mg of cells per ml of culture medium;

permitting said strain to grow until said density increases between 3 and 5 times; and subculturing said strain, wherein a density of said subculture is between 3 and 8 mg of cells per ml of culture medium.

4. A process according to claim 2, wherein said auxin is selected from the group consisting of 2,4-dichlorophenoxyacetic acid, 1-napthaleneacetic acid and 2-naphthoxyacetic acid.

5. A process according to claim 2, wherein said auxin is 2-naphthoxyacetic acid, at a concentration of between 2.5 and 7 $\mu$mole/liter.

6. A process according to claim 2, wherein said auxin is 2-naphthoxyacetic acid at a concentration of 5 $\mu$mole/liter.

7. A process according to claim 3, wherein prior to said subculturing said cellular aggregates are sieved so as to preserve only those whose size does not exceed 500 $\mu$m.

8. A process according to claim 3, further comprising replacing said culture medium each week by subculturing.

9. A process for developing embryos from a proembryogenic cell line intended for the regeneration of vines, comprising:

culturing said cell line for between 3 and 7 days in a standard liquid culture medium for culturing plant cells at an initial inoculation density; and replacing by subculturing said culture medium daily until plantlets are obtained in which two generally green, well developed cotyledons and a long root can be distinguished, wherein during each replacement of said culture medium during subculturing, the density of the culture is readjusted to the initial inoculation density.

10. A process according to claim 9, wherein the appropriate culture medium is auxin-free.

11. A process according to claim 9, wherein said initial inoculation density is between 0.5 and 2 $\mu$l/ml.

12. A process according to claim 9, wherein said initial inoculation density is between 1 and 2 $\mu$l/ml.

13. A process according to claim 9, wherein said strain comprises, during the initial inoculation, cellular aggregates between 200 and 500 $\mu$m in size.

14. A process according to claim 13, wherein said cellular aggregates are obtained by culturing said strain in a liquid culture medium in the presence of an auxin, further comprising the steps of:

filtering said cellular aggregates using a filter having a porosity of about 500 $\mu$m in order to remove cellular aggregates having a size greater than about 500 $\mu$m;

filtering said cellular aggregates using a filter having a porosity of about 200 $\mu$m in order to remove cellular aggregates having a size less than about 200 $\mu$m; and washing said filtered cellular aggregates with an auxin-free liquid culture medium to remove substantially all auxin.

15. A process according to claim 9, wherein said strain is a cell line of proembryogenic cellular aggregates deposited under No. PL92042917 and variants and derived cultures having preserved comparable proembryogenic properties.

16. A process according to claim 9, wherein said strain can develop at least 100 embryos per mg of cells.

17. A process for developing embryos according to claim 9 from a culture of proembryogenic vine cells deposited under No. PL92042917 and variants and derived cultures having preserved comparable proembryogenic properties intended for the regeneration of vines.

18. A process according to claim 17, wherein said culture can develop at least 100 embryos per mg of cells.

19. A culture of a proembryogenic cell line deposited under No. PL92042917.

* * * * *